United States Patent
Rabe et al.

(10) Patent No.: US 6,482,398 B1
(45) Date of Patent: *Nov. 19, 2002

(54) TRANSFER-RESISTANT LIP COMPOSITIONS

(75) Inventors: Thomas Elliot Rabe, Baltimore, MD (US); Lee Ellen Drechsler, Cincinnati, OH (US); Edward Dewey Smith, III, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/399,411

(22) Filed: Sep. 20, 1999

Related U.S. Application Data

(63) Continuation of application No. 08/545,976, filed on Oct. 20, 1995, now abandoned, which is a continuation-in-part of application No. 08/481,776, filed on Jun. 7, 1995, now abandoned.

(51) Int. Cl.[7] .......................... A61K 7/025; A61K 7/027

(52) U.S. Cl. .............................. 424/64; 424/64; 424/63; 424/401

(58) Field of Search ............................. 424/64, 63, 401

(56) References Cited

U.S. PATENT DOCUMENTS

| | | | | |
|---|---|---|---|---|
| 5,183,589 A | * | 2/1993 | Brunetta et al. ............. | 252/308 |
| 5,505,937 A | * | 4/1996 | Castrogiovanni et al. ..... | 424/64 |
| 6,045,782 A | * | 4/2000 | Krog et al. .................... | 424/64 |
| 6,033,650 A | * | 5/2000 | Calello ......................... | 424/64 |

* cited by examiner

*Primary Examiner*—Russell Travers
*Assistant Examiner*—Shanam Sharareh
(74) *Attorney, Agent, or Firm*—Dara M. Kendall; Tara M. Rosnell; Steven W. Miller

(57) ABSTRACT

The present invention relates to stable lip compositions comprising a first material and a second material wherein the second material is entrapped throughout the first material. The first and second materials are sufficiently incompatible with each other wherein when the composition is applied to the lips, the second material separates from said first material forming a barrier layer over the first material deposited on the lips. Using such a composition eliminates having to individually apply a barrier layer over the lipstick previously applied to the lips.

19 Claims, No Drawings

US 6,482,398 B1

TRANSFER-RESISTANT LIP COMPOSITIONS

CROSS-REFERENCE TO RELATED APPLICATION

This application is a continuation of applicant's copending application Ser. No. 08/545,976, filed Oct. 20, 1995 now abandoned.

TECHNICAL FIELD

The present invention relates to stable lip compositions comprising a first material and a second material wherein the second material is entrapped throughout the first material. The first and second materials are sufficiently incompatible with each other wherein when the composition is applied to the lips, the shearing forces created causes the second material to separate from the first material forming a barrier layer over the first material deposited on the lips. Using such a composition eliminates having to individually apply a barrier layer over the lipstick previously applied to the lips.

BACKGROUND OF THE INVENTION

Lip treatment products whose primary purpose is to extend wear, improve the blot transfer resistance and heighten the gloss of said lipstick are well known in the art. Some of these products such as overcoats utilize a variety of polymeric fluids and film forming technologies to form a barrier layer that avoids transference of the lipstick it is applied over. Examples of such compositions are disclosed in Japanese Patent Application Number HEI 5[1993]-221829published Aug. 31, 1993 and copending U.S. Ser. No. 08/361,246, filed Dec. 21, 1994; and now published as WO 96/019,185 both incorporated herein by reference. Although said overcoat products can be effective in preventing inadvertent transfer onto objects, they do require separate application over the pigmented lip composition applied to the lips. It is, therefore, advantageous to provide a product which combines these two separate application steps into one single step.

SUMMARY OF THE INVENTION

The present invention is a lip composition comprising a first and second material, wherein the first material has a second material entrapped throughout it. Said first and second materials are sufficiently incompatible where upon application of the present composition to the lips, the shearing forces created cause the second material to separate from the first material forming a barrier layer over the first material deposited on the lips.

Therefore, an objective of the present invention is to provide a composition wherein the second material forms a barrier, thereby preventing inadvertent transference of the first material to objects such as tableware and clothing contacting the lips. Another object of the present invention is to provide a barrier layer over a pigmented lip composition in a single step. Still another object of the present invention is to provide a composition having desirable application and feel characteristics as well as improve luster and shine of the composition once applied to the lips. A last object of the present invention is to provide processing steps for making such compositions.

The composition of the present invention can take a number of forms often associated with lip composition, including solid sticks, creams and balms. Unless otherwise indicated, all percentages disclosed herein are by total weight of the composition.

DETAILED DESCRIPTION OF THE INVENTION

1. First Material

The first material or continuous material of the present composition comprises lipophilic materials selected from the group consisting of waxes, volatile oils, nonvolatile oils and mixtures thereof wherein the oils are compatible with said was when said was is liquified. The first material comprises from about 30% to about 95%, preferably from about 50% to about 85%, and most preferably from about 50% to about 60% of the composition.

Waxes act as solidifying agents thereby assisting in forming solid structures such as "bullet" shaped lipsticks. Waxes as used herein are defined as organic compounds or mixtures of high molecular weight substances, that are thermoplastic, forming a solid mass at ambient temperature/room temperature. As used herein wax refers to single type of wax or mixtures of waxes.

Said waxes include hydrocarbons or esters of fatty acids and fatty alcohols and are derived from natural, synthetic and mineral sources. Such waxes are disclosed in Warth, *Chemistry and Technology of Waxes*, Parts 1 and 2, 1956, Reinhold Publishing Corporation, Natural waxes can be of animal origin, such as beeswax, spermaceti, lanolin, shellac wax, of vegetable origin, e.g. carnauba, candelilla, bay berry, sugar cane wax, or of mineral origin, e.g. ozokerite, ceresin, montan, paraffin, microcrystalline wax, petroleum and petrolatum wax. Synthetic waxes include polyol ether-esters such as carbowax and hydrocarbon-type waxes, silicone waxes and polyethylene wax having melting points greater than about 40° C. The waxes most useful herein have melting points from about 55° C. to about 110° C. and are selected from the $C_8$ to $C_{50}$ hydrocarbon waxes.

The waxes preferred for use in the present compositions are selected from the group consisting of candelilla, beeswax, beeswax having free fatty acids removed (modified beeswax), carbauba, spermaceti, montan, ozokerite, ceresin, paraffin, bayberry, castor waxes, synthetic waxes, microcrystalline waxes, silicone waxes (modified to be compatible with other first materials) and mixtures thereof. More preferably the waxes are selected from the group consisting of microcrystalline, spermaceti, candelilla, modified beeswax, carnanuba, oxokerite, paraffin, ceresin, silicon waxes and mixtures thereof. Most preferably, the waxes are selected from the group consisting of candelilla, oxokerite, paraffin, carnanuba, wax and mixtures thereof.

The volatile and nonvolatile oils of the present invention have a number of functional purposes, for example application, adhesion, yield, gloss and perhaps most importantly occlusive moisturization, generally. Said oils are liquid at ambient temperature and include esters, triglycerides, hydrocarbons, silicones and mixtures thereof.

Volatile oils, particularly those selected from the group consisting of volatile hydrocarbons, polydimethylsiloxanes, cyclic polydimethyl siloxane and mixtures thereof are incorporated into the lipstick compositions to provide more rigid lipstick films due to higher wax to oil ratio in the film once the volatile component has evaporated. Particularly useful are the volatile oils that are hydrocarbon based. Said volatile oils are selected from the group consisting of saturated branched hyrodcarbons, unsaturated branched hydrocarbons, saturated linear hydrocarbons, unsaturated linear hydrocarbons and mixtures thereof having from about from about 8 to about 30 carbon atoms per molecule, preferably from about 8 to about 20 carbon atoms per molecule, and most preferably from about 8 to about 14 carbon atoms per molecule. The rigid film produced by the addition of a volatile oil reduces the amount of lipstick that is transferred to other objects. In spite of the teaching in the art, such as European Patent Publication 602905, published Jun. 22, 1994, regarding the use of a volatile oils to make rigid films, the present invention is practically better. The present invention delivers a barrier layer over said rigid film thereby providing the user with a long lasting moist and lubricious feeling on the lips which the rigid film alone cannot create.

As previously mentioned, this invention also envisions the addition of nonvolatile oils. Specific nonvolatile oils useful in the present invention include caprylic triglycerides; capric triglycerides; isostearic triglycerides; adipic triglycerides; wheat germ oil; hydrogenated vegetable oils, petrolatum; branched-chain hydrocarbons; alcohols and esters; castor oil; lanolin oil; corn oil; cottonseed oil; olive oil; palm kernel oil; rapeseed oil; safflower oil; jojoba oil; evening primrose oil; avocado oil; mineral oil; sheabutter; octylpalmitate; maleated soybeam oil; glycerol trioctanoate; diisopropyl dimerate; silicone oils including dimethicone, phenyl dimethicone, cyclomethicone, poly(perfluoroalkyl) siloxanes, linear and cyclic polyalkyl siloxanes and mixtures thereof. Preferable oils used in the present invention are selected from the group consisting of caprylic triglycerides, capric triglycerides, isostearic triglyceride, castor oil, adipic triglyceride, dimethicone, octyl dodecanol, oleyl alcohol, hydrogenated vegetable oils, maleated soybean oil, lanolin oil, polybutene, oleyl alcohol; hexadecyl alcohol wheat germ glycerides and mixtures thereof. The individual oils or the aggregate of the oils selected should be soluble with the liquefied waxes selected for use herein. Therefore, oils have a solubility parameter from about 5 to about 10. The respective solubility parameters for waxes and oils are reported in "Cosmetics & Toiletries", Vol 103, October 1998; incorporated herein by reference.

Emollients useful in the present invention are found in The C.T.F.A. Comsetic Ingredient Handbook, pages 572–575, 1992; herein incorporated by reference. Said emollients include lanolin, synthetic lanolin derivatives, modified lanolins, isopropyl palmitate, isononyl isononanoate, isopropoyl isostearate, cetyl ricinoleate, octyl palmitate, cetyl ricinoleate, glyceryl trioctanoate, diisopropyl dimerate, propylene glycol, myristyl acetate, isopropyl myristate, diethyl sebacate; diisopropyl adipate; tocopheryl acetate; tocopheryl linoleate; hexadecyl stearate; ethyl lactate; cetyl lactate, cetyl oleate, octyl hydroxystearate; octyl dodecanol, decyl oleate, propylene glycol ricinoleate, isopropyl lanolate, pentaerythirtyl tetrastearate, neopentylglycol dicaprylate/dicaprate, hydrogenated coco-glycerides, isotridecyl isononanoate, isononyl isononanoate, myristal myristate, triisoetyl citrate, cetyl alcohol, octyl dodecanol, oleyl alcohol and mixtures therefor. Particularly useful emollients are selected from the group consisting of lanolin, isopropyl isostearate, cetyl lactate, octyl hydroxystearate and mixture thereof.

Humectants useful in the present invention include those as disclosed in The C.T.F.A. Cosmetic Ingredient Handbook, page 567, 1992; herein incorporated by reference. Occulsives useful in the present invention are likewise found in the C.T.F.A. Cosmetic Ingredient Handbook, at pages 578–580; herein incorporated by reference.

2. Second Material

The second material of the present invention is selected from the group consisting of volatile materials having a vapor pressure of greater than about 10 mm Hg at 30° C., non-volatile materials and mixtures thereof wherein said second material as a viscosity from about 0.5 to about 5,000 centistokes. In the present invention, the second material comprises from about 5% to about 70%, preferably 15% to about 50%, and most preferably from about 30% to about 40% of the composition.

The second material of the present invention comprises a single material or an aggregate of material which are incompatible with the first material. By incompatible it is meant that the second material is dispersed throughout the liquefied first material, similar to an emulsion-phase. Upon solidification, this second material eventually is entrapped within the first material, preferably in an even distriution; i.e. small particles or droplets distributed throughout the first material. The second material remains entrapped within the first material until the composition experiences shearing forces created by application of the composition on the lips. At this point the entrapped second material has no physical barriers to prevent its coalescence wherein the second material spreads over the first material, essentially forming a barrier layer over the first material.

It should be noted, however, some of the individual components making up the first and second materials may exhibit some degree of compatibility with components of the opposite material. first and second materials. Volatile oils are one such example of a component that may partition between the first and second materials. However, in the present invention any component demonstrating at least some compatibility for both the first and second materials will not exhibit compatibility to the degree that its inclusion makes the first and second materials completely compatible. Furthermore, while the second material is incompatible with the first material, said second material may be an aggregate of materials wherein some and possibly all of those materials are incompatible with each other.

The existence of a second material entrapped within said first material is readily detectable by an artisan using routine analytical methods including centrifugation of the emulsion wherein two separate layers form, microscopy of solid compositions wherein the entrapped second material is directly observed within the solid lipophilic material continuous phase.

By "volatile" it is meant that the vapor pressure of said volatile oil is less than about 10 mm Hg, preferably less than about 1 mm Hg, and most preferably less than about 0.5 mm Hg at 30° C. as measured using analytical means known to those skilled in the art. Said second material of the present invention has a viscosity from about 0.5 to about 5,000 centistokes (cSt), preferably from about 1 to about 500 cSt, most preferably from about 10 to about 100 cSt. Although the second material of the present invention may be either volatile or non-volatile, non-volatile materials are preferred.

Said second material of the present invention preferably is close to being optically transparent or translucent at the thickness that results from application of the said composition to the lips. The second material which forms the barrier layer or film over the first material on the lips is thus undetectable to the naked eye after the composition is applied to the lips so as not to hinder the presentation of the color of the present composition on the lips. This optical transparency is measured in terms of a film contrast ratio. The contrast ratio is preferably between 0.00 and 0.20 for a 1 mil (0.001 inch) thick film of the said material. The contrast ratio measurement technique is as follows:

1. Place a Type 2A Opacity Chart (The Leneta Company, Ho-Ho-Kus, N.J., USA) onto a flat vacuum table;

2. Draw down a 0.001" thick film of the said material using a 0.001" Byrd Film Applicator (MCD Industries, Medfield, Mass., USA) onto the opacity chart, coating both the white and black regions of the chart; and
3. Measure the Y-value over the black region and the Y-value over the white region of the chart using a spectrophotometer (e.g. Microflash, Datacolor International, Lawrenceville, N.J., USA).

The contrast ratio is defined Y-value (black)/Y-value (white).

As previously mentioned the second material forms a barrier layer over the first material for the composition is applied to the lips. Therefore, it is critical that the second material separates from the first material and easily spreads over the lips by routine application of the composition to form said barrier layer without receding back into the first material or forming individual droplets over the first material. The ability of a second material to spread and remain in such a state is determined by the surface tension of the second material and by the surface tension of the underlying first material. The second material is found to be spreadable over a surface when its surface tension is equal to or below the critical surface tension for wetting of the surface. The critical surface tension for wetting a surface, first defined by Fox and Zisman, is equal to the surface tension of the second material which just exhibits a zero contact angle on the surface; see H. W. Fox and W. A. Zisman, J. Colloid Sci., 5, 514 (1950), H. W. Fox and W. A. Zisman, J. Colloid Sci., 7, 109 (1952) and H. W. Fox and W. A. Zisman, J. Colloid Sci., 7, 428 (1952), all incorporated herein by reference. Since this critical surface tension of wetting can vary with composition of the first material, a second material with a surface tension equal to or below the critical surface tension of wetting must be chosen for each particular first material composition. Such a second material would exhibit a contact angle of about zero when placed on a flat, drawn-down film of the composition's first material. The surface tension of the second material of the present invention is less than about 35 dynes/cm, preferably less than about 30 dynes, most preferably less than about 25 dynes/cm.

Second materials useful in the present invention include poly(organosiloxane) fluids conforming to the formula:

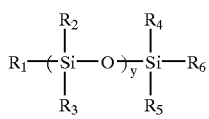

wherein the end groups $R_1$ and $R_6$ are independently selected from the group consisting of hydroxyl groups, lower alkyl groups having carbon chain lengths from about $C_1$ to about $C_6$ and mixtures thereof, preferably methyl groups and the non-end groups $R_2$, $R_3$, $R_4$ and $R_5$ are independently selected from methyl groups, fluoroalkyl groups, phenyl groups and mixtures thereof.

The poly(organosiloxane) fluids with non-end groups ($R_2$, $R_3$, $R_4$ and $R_5$) comprising methyl groups are known in the art and provide the final product with a relatively non-lipohilic character. Commercially available non-volatile silicone fluids having such non-end groups include those available from Dow Corning as the 200 Fluids, and those available from General Electric as SF-96 Series.

Silicone fluids with non-end groups comprising fluoroalkyl grousp are also useful herein. It is preferable, however, that the fluorine atom is attached to alkyl groups having a $C_3$ to $C_8$ chain length wherein the fluorine atom is attached to attached to said alkyl group at a point no closer than third carbon atoms from the silicone/carbon bond. Commercially available non-volatile silicone fluids having such non-end groups include those available from Dow Corning as the 1265 Fluid series, and those available from General Electric as the SF-1153 Series, most preferred is the 1265 Fluid Series, most preferably those of having a viscosity from about 100 cSt to about 350 cSt.

Silicone fluids with the non-end groups comprising alkyl groups are also useful in the present invention. The alkyl groups which are particularly useful in the present invention are phenyl groups. Particularly useful allyl-substituted silicone fluids commercially available are available as the 556 Series from Dow Corning.

Preferable poly(organosiloxane) fluids of the present invention are selected from the group consisting of poly (dimethylsiloxane) fluids, poly(phenylmethylsiloxane) fluids, poly(fluoroalkylmethylsiloxane) fluids, the copolymers of said fluids and mixtures thereof. More preferred fluids are selected from the group consisting of poly (dimethylsiloxiane) fluids, their copolymers and mixtures thereof. Most preferred are poly(dimethylsiloxane) fluids and their copolymers, preferably selected from the group consisting of dimethicone, phenyl dimethicone, phenyl trimethicone and mixtures thereof.

Non-silicone fluids also useful as a second material of the present invention include perfluoropolyethers of general formula:

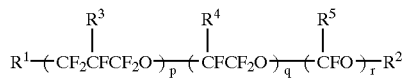

wherein $R^1$ though $R^5$ are selected from the group consisting of fluorine atoms, perfluoroalkyl groups, oxyperfluoroalkyl groups and mixtures thereof, the value of p, q, and r collectively are of a value such that the perfluoropolyether molecular weight is from about 500 to about 10,000 wherein p, q and r may be equal. A preferred perfluoropolyether is the commercially available product known as Fomblin HC-01, -02, -03, and -04, HC-25 and HC-R available from Montefluosu of Milano, Italy. Non-volatile perfluoropolyethers are preferred.

C. Optional Ingredients

Compositions of the present invention further include optional ingredients which may be added to the compositions disclosed above to provide various consumer desirable characteristics to the product. Said optional ingredients include those routinely used in the cosmetic arts to produce a specific cosmetic effect which is deemed desirable.

Surfactants may be used in the present invention insofar as they do not sufficiently stabilize the second material entrapped within the first material or allowing said second material to separate from the first material upon application to the lips. Surfactants are well known to those skilled in the art of lipstick making in order to enhance dispersability of pigments and other solid materials like mica and talc, stabilize liquid dispersed phases such as water, glycerine and glycols, provide skin benefits such as emolliency, and skin feel modifiers; i.e. the right combination can make the stick less hard. Anionic surfactants, nonionic surfactants, cationic surfactants, amphoteric surfactants and mixtures thereof are suitable for use. The more common surfactants used in the present invention include those found in the C.T.F.A. Cosmetic Ingredient Handbook, pages 587–592, 1992; herein incorporated by reference. Some of the more commonly used ones include ethoxylated castor oil, lecithin, fatty acids and salts of fatty acids (sodium stearate, stearic acid, oleic acid, potassium stearate, zinc stearate), fatty alcohols (oleyl alcohol, e.g.), ascorbyl palmitate, oxidized waxes, mono and diglycerides (glyceryl oleate), lauroyl lysine, cetyl lactate and mixtures thereof.

In addition to surfactants other ingredients such as preservatives, sunscreens, UV absorbers, anti-oxidants, flavorings, perfumes, colorants, dyes and other ingredients routinely used in the art. In the case of dyes and colorants which are incorporated into the first material, it is important that the first and second materials are sufficiently incompatible to avoid tinting or coloring the second

EXAMPLES

Example 1:

| Ingredient | Weight Percent (%) |
|---|---|
| Candelilla Wax | 4.70 |
| Carnauba Wax | 3.40 |
| Ozokerite | 4.30 |
| Paraffin | 2.10 |
| Lanolin | 4.30 |
| Isopropyl Isostearate | 12.80 |
| Cetyl Lactate | 1.70 |
| Octyl Hydroxystearate | 8.50 |
| Ascorbyl Palmitate | 0.70 |
| Propyl Paraben | 0.16 |
| Vitamin E Acetate | 0.04 |
| Castor Oil | 34.00 |
| Red #7 Ba Lake | 2.60 |
| Red #6 Ca Lake | 2.10 |
| Hematite | 4.70 |
| Titanium Dioxide | 8.90 |
| Perfluoropolyether* | 5.00 |

*available as Fomblin HC/25 from Ausimont SPa

Example 2:

| Ingredient | Weight Percent (%) |
|---|---|
| Candelilla Wax | 4.20 |
| Carnauba Wax | 3.10 |
| Ozokerite | 3.80 |
| Paraffin | 1.90 |
| Lanolin | 3.80 |
| Isopropyl Isostearate | 11.50 |
| Cetyl Lactate | 1.50 |
| Octyl Hydroxystearate | 7.60 |
| Ascorbyl Palmitate | 0.70 |
| Propyl Paraben | 0.06 |
| Vitamin E Acetate | 0.04 |
| Castor Oil | 30.40 |
| Red #7 Ba Lake | 2.30 |
| Red #6 Ca Lake | 1.90 |
| Hematite | 4.20 |
| Titanium Dioxide | 8.00 |
| 10 cSt Dimethicone* | 15.00 |

*available as Dow Corning 200 Fluid

Example 3:

| Ingredient | Weight Percent (%) |
|---|---|
| Candelilla Wax | 3.50 |
| Carnauba Wax | 2.50 |
| Ozokerite | 3.20 |
| Paraffin | 1.60 |
| Lanolin | 3.20 |
| Isopropyl Isostearate | 9.30 |
| Cetyl Lactate | 1.30 |
| Octyl Hydroxystearate | 6.30 |
| Ascorbyl Palmitate | 0.50 |
| Propyl Paraben | 0.07 |
| Vitamin E Acetate | 0.03 |
| Castor Oil | 25.00 |
| Red #7 Ba Lake | 1.90 |
| Red #6 Ca Lake | 1.50 |
| Hematite | 3.50 |
| Titanium Dioxide | 6.6 |
| 50 cSt Dimethicone* | 30.00 |

*available as Dow Corning 200 Fluid

Example 4:

| Ingredient | Weight Percent (%) |
|---|---|
| Candelilla Wax | 4.00 |
| Beeswax | 2.00 |
| Ozokerite | 3.20 |
| Paraffin | 1.60 |
| Lanolin | 3.20 |
| Isopropyl Isostearate | 9.30 |
| Cetyl Lactate | 1.30 |
| Octyl Hydroxystearate | 6.30 |
| Ascorbyl Palmitate | 0.50 |
| Propyl Paraben | 0.07 |
| Vitamin E Acetate | 0.03 |
| Castor Oil | 25.00 |
| Red #7 Ba Lake | 1.90 |
| Red #6 Ca Lake | 1.50 |
| Hematite | 3.50 |
| Titanium Dioxide | 6.60 |
| 50 cSt Dimethicone* | 15.00 |
| Perfluoropolyether** | 15.00 |

*available as Dow Corning 200 Fluid
**available as Fomblin HC/25 from Ausimont SPa Example 5:

| Ingredient | Weight Percent (%) |
|---|---|
| Candelilla Wax | 3.00 |
| Carnauba Wax | 3.00 |
| Ozokerite | 4.80 |
| Lanolin | 3.20 |
| Isopropyl Isostearate | 9.30 |
| Cetyl Lactate | 1.30 |
| Octyl Hydroxystearate | 6.30 |
| Ascorbyl Palmitate | 0.50 |
| Propyl Paraben | 0.07 |
| Vitamin E Acetate | 0.03 |
| Castor oil | 25.0 |
| Red #7 Ba Lake | 1.90 |
| Red #6 Ca Lake | 1.50 |
| Hematite | 3.50 |
| Titanium Dioxide | 6.60 |
| 50 cSt Phenylmethicone* | 30.00 |

*available as Dow Corning 556 Fluid

Example 6:

| Ingredient | Weight Percent (%) |
| --- | --- |
| Candelilla Wax | 2.70 |
| Carnauba Wax | 2.00 |
| Ozokerite | 2.50 |
| Paraffin | 1.30 |
| Lanolin | 2.50 |
| Isopropyl Isostearate | 7.40 |
| Cetyl Lactate | 1.00 |
| Octyl Hydroxystearate | 4.90 |
| Ascorbyl Palmitate | 0.40 |
| Propyl Paraben | 0.05 |
| Vitamin E Acetate | 0.05 |
| Castor Oil | 19.70 |
| Red #7 Ba Lake | 1.50 |
| Red #6 Ca Lake | 1.20 |
| Hematite | 2.70 |
| Titanium Dioxide | 5.10 |
| 50 cSt Dimethicone* | 45.00 |

*available as Dow Corning 200 Fluid

Example 7:

| Ingredient | Weight Percent (%) |
| --- | --- |
| Candelilla Wax | 2.70 |
| Carnauba Wax | 2.00 |
| Ozokerite | 2.50 |
| Paraffin | 1.20 |
| Lanolin | 2.50 |
| Isopropyl Isostearate | 7.40 |
| Cetyl Lactate | 1.00 |
| Octyl Hydroxystearate | 4.90 |
| Ascorbyl Palmitate | 0.40 |
| Propyl Paraben | 0.15 |
| Vitamin E Acetate | 0.05 |
| Castor Oil | 25.00 |
| Red #7 Ba Lake | 1.50 |
| Red #6 Ca Lake | 1.20 |
| Hematite | 2.70 |
| Titanium Dioxide | 4.80 |
| 50 cSt Dimethicone* | 20.00 |
| 50 cSt Phenylmethicone** | 20.00 |

*available as Dow Corning 200 Fluid
**available as Dow Corning 556 Fluid

Example 8:

| Ingredient | Weight Percent (%) |
| --- | --- |
| Candelilla Wax | 2.70 |
| Carnauba Wax | 2.00 |
| Ozokerite | 2.50 |
| Paraffin | 1.20 |
| Lanolin | 2.50 |
| Isopropyl Isostearate | 7.50 |
| Cetyl Lactate | 1.00 |
| Octyl Hydroxystearate | 4.90 |
| Ascorbyl Palmitate | 0.40 |
| Propyl Paraben | 0.05 |
| Vitamin E Acetate | 0.05 |
| Castor Oil | 19.70 |
| Red #7 Ba Lake | 1.50 |
| Red #6 Ca Lake | 1.20 |
| Hematite | 2.70 |
| Titanium Dioxide | 5.10 |
| 300 cSt Fluorosilicone* | 45.00 |

*available as Dow Corning 1265 Fluid

Example 9:

| Ingredient | Weight Percent (%) |
| --- | --- |
| Candelilla Wax | 1.50 |
| Carnauba Wax | 1.60 |
| Ozokerite | 1.30 |
| Paraffin | 0.70 |
| Lanolin | 1.40 |
| Isopropyl Isostearate | 4.20 |
| Cetyl Lactate | 0.50 |
| Octyl Hydroxystearate | 2.00 |
| Ascorbyl Palmitate | 0.20 |
| Propyl Paraben | 0.04 |
| Vitamin E Acetate | 0.06 |
| Castor Oil | 10.70 |
| Red #7 Ba Lake | 0.80 |
| Red #6 Ca Lake | 0.70 |
| Hematite | 1.50 |
| Titanium Dioxide | 2.80 |
| 50 cSt Dimethicone* (99.5% total) | 70.00 |

*available as Dow Corning 200 Fluid

Examples 1–9 and assembled according to the following instructions:

Combine the pigments are castor oil in a vessel with stirring until incorporating the pigments into said castor oil. Pass the mixture through a 3-roll mill three times yielding a dispersion of pigment particles in oil; hereinafter referred to as the slurry.

Except for the second material, combine all the remaining ingredients in a vessel equipped with heating and mixing. Heat the combination to about 95° C., holding there for a sufficient times wherein said ingredients are in a liquid form. While maintaining the heat, stir the combination of ingredients for about 30 minutes, obtaining a transparent yellow fluid. Cool the combination to about 21° C. until forming a pale yellow waxy solid; hereinafter referred to as the base.

Combine the pigment slurry and the base, hereinafter collectively referred to as the first material, with the second material in order of the highest weight percentage of the composition first. Heat this combination to about 90° C. until the combination becomes liquid. Cease heating the combination and mix for about 3 minutes at 10,000 RPM using a Janke & Kunkel Ultra-Turrax turbine mixer. Pour the combination immediately into a room temperature aluminum bullet mold. Cool the filled mold until the combination is solid. Remove the solid composition from the molds and place in suitable cosmetic packaging.

Example 10:

| Ingredient | Weight Percent (%) |
| --- | --- |
| Ceresin Wax | 2.70 |
| Carnauba Wax | 2.00 |
| Microcrystalline Wax | 2.50 |
| Paraffin | 1.20 |
| Tricontanyl PVP | 2.50 |
| Isoeicosane | 7.50 |
| Glyceryl Linoleate | 1.00 |
| Octyl Methoxycinnamate | 4.90 |
| Ascorbyl Palmitate | 0.40 |
| Propyl Paraben | 0.05 |
| Vitamin E Acetate | 0.05 |
| Red #7 Ba Lake | 1.50 |
| Red #6 Ca Lake | 1.20 |
| Hematite | 2.70 |

-continued

| Ingredient | Weight Percent (%) |
| --- | --- |
| Titanium Dioxide | 5.10 |
| 50 CSt Dimethicone* | 19.70 |
| Perfluoropolyether** | 45.00 |

*available as Dow Corning 200 Fluid
**available as Fomblin HC/4 from Ausimont SPa Example 10 is made according to the following instructions:

Combine the pigments and dimethicone in a vessel equipped with stirring. After incorporating the pigments in the dimethicone, pass the mixture through a 3-roll mill three times yielding a dispersion of pigment particles in dimethicone; hereinafter referred to as the slurry.

Except for the perfluoropolyether fluid and the slurry, combine all the remaining ingredients in a vessel equipped with heating and mixing. Heat the remaining ingredients to about 95° C., holding there for a sufficient times until said ingredients are in a liquid form. While maintaining this temperature, stir said ingredients for about 30 minutes, or until obtaining a transparent yellow fluid. Cool the combination to about 21° C. until forming a pale yellow waxy solid; hereinafter referred to as the base.

Combine the pigment slurry and the base, hereinafter collectively referred to as the first material, with the perfluoropolyether fluid, the second material. Heat the composition to about 90° C. until it becomes liquid. Cease heating the composition and mix for about 3 minutes at 10,000 RPM using a Janke & Kunkel Ultra-Turrax turbine mixer. Pour the composition immediately into a room temperature aluminum bullet mold. Cool the filled mold until the composition is solid. Remove the solid composition from the molds and place in suitable cosmetic packaging.

Example 11:

| Ingredient | Weight Percent (%) |
| --- | --- |
| Candelilla Wax | 1.12 |
| Carnauba Wax | 4.27 |
| Ozokerite | 6.71 |
| Paraffin | 0.94 |
| Acetylated Lanolin | 2.37 |
| Isopropyl Isostearate | 5.62 |
| Cetyl Alcohol | 0.75 |
| Cetyl Lactate | 0.75 |
| Octyl Hydroxystearate | 3.19 |
| Ascorbyl Palmitate | 0.19 |
| Propyl Paraben | 0.04 |
| Vitamin E Acetate | 0.02 |
| Castor Oil | 16.63 |
| Pigments | 6.60 |
| Stainers | 0.26 |
| Mica | 3.34 |
| Isododecane* | 12.00 |
| 50 cSt Dimethicone** | 35.20 |

*available as Permethy 99A from Presperse, Inc.
**available as Dow Corning 200 Fluid Example 11 is made according to the following instructions:

Combine the pigments and castor oil in a vessel with stirring until incorporating the pigments into said castor oil. Pass the mixture through a 3-roll mill three times yielding a dispersion of pigment particles in oil; hereinafter referred to as the slurry.

Except for the second material, and the isododecane, combine all the remaining ingredients in a vessel equipped with heating and the mixing. Heat the combination to about 95° C., holding there for a sufficient times wherein said ingredients are in a liquid form. While maintaining the heat, stir the combination of ingredients for about 30 mintues, obtaining a transparent yellow fluid. Cool the combination to about 21° C. until forming a pale yellow waxy solid; hereinafter referred to as the base.

Combine the pigment slurry and the base, hereinafter collectively referred to as the first material, with the second material in order of the highest weight percentage of the composition first. Heat this combination to about 90° C. until the combination becomes liquid. Cease heating the combination and mix for about 3 minutes at 10,000 RPM using a Janke & Kunkel Ultra-Turrax turbine mixer. Cool the combination to about 70° C., add the isododecane, and stir for 1 minute using a propeller-type mixer. Pour the combination immediately into chilled (5° C.) aluminum bullet molds. Cool the filled molds until the combination is solid. Remove the solid composition from the molds and place in suitable cosmetic packaging.

What is claimed is:

1. A lipstick composition comprising:
   a. from about 30% to about 95% of a first material wherein said first material is lipophilic and is selected from the group consisting of waxes, volatile oils, nonvolatile oils and mixtures thereof and wherein the oils are compatible with said wax when said wax is liquified; and
   b. from about 5% to about 70% of a second nonvolatile material selected from the group consisting of polydimethylsiloxane fluids, poly(phenylmethylsiloxane) fluids, poly(fluoroalkylmethylsiloxane) fluids, perfluoropolyethers, copolymers thereof, and mixtures thereof, the second material having a viscosity from about 10 to about 5,000 centistokes;
   wherein said second material is incompatible with said first material and is entrapped in said first material where upon application of said lipstick composition to the lips, said second material separates from said first material forming a barrier layer over said first material deposited on the lips and wherein said composition is free of surfactants that would sufficiently stabilize the second material entrapped within the first material.

2. The composition of claim 1 wherein said waxes are selected from the group consisting of candelilla, beeswax, beeswax having free fatty acids removed, carnauba, spermaceti, montan, ozokerite, ceresin, paraffin, bayberry, castor waxes, synthetic waxes, microcrystalline waxes, silicone waxes and mixtures thereof.

3. The composition of claim 1 wherein said non-volatile oils are selected from the group consisting of caprylic triglycerides, capric triglcerides, isostearic triglyceride, castor oil, adipic triglyceride, dimethicone, octyl dodecanol, oleyl alcohol, hydrogentated vegetable oils, maleated soybeam oil, lanolin oil, polybutene, oleyl alcohol; hexadecyl alcohol wheat germ glycerides and mixtures thereof.

4. The composition of claim 1 wherein said volatile oils are selected from the group consisting of hydrocarbon oils, dimethylsiloxanes, cyclic polydimethyl siloxane and mixture thereof having from about 8 to about 30 carbon atoms per molecule.

5. The composition of claim 4, wherein said hydrocarbon oils comprise oils selected from the group consisting of saturated branched hydrocarbons, unsaturated branched hydrocarbons, saturated linear hydrocarbons unsaturated linear hydrocarbons and mixtures thereof having from about 8 to about 14 carbon atoms per molecule.

6. The composition of claim 1 wherein said second material has a vapor pressure less than about 0.5 mm Hg at 30° C.

7. The composition of claim 1 wherein said second material is optically transparent.

8. The composition of claim 1 wherein said second material has a surface tension of less than about 35 dynes/cm.

9. The composition of claim 8 wherein said second material has a surface tension of less than about 25 dynes/cm.

10. The composition of claim 1 comprising from about 50% to about 85% of said first material and from about 15% to about 50% of said second material.

11. The composition of claim 10 comprising from about 50% to about 60% of said first material and from about 30% to about 40% of said second material.

12. The composition of claim 1 wherein said second material has a viscosity from about 10 to about 500 centistokes.

13. The composition according to claim 1 wherein said second material is a poly(dimethylsiloxane) fluid, its copolymers and mixtures thereof.

14. The composition according to claim 13 wherein said second material is dimethicone.

15. The composition according to claim 1 wherein the said second material is a perfluoropolyether of general formula:

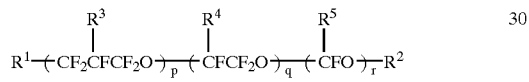

wherein $R^1$ through $R^5$ are selected from the group consisting of fluorine atoms, perfluoroalkyl groups, oxyperfluoroalkyl groups and mixtures thereof, the value of p, q, and r collectively are of a value such that the perfluoropolyether molecular weight is from about 500 to about 10,000 wherein p, q and r may be equal.

16. The composition according to claim 15 wherein said perfluoropolyether is non-volatile.

17. A lipstick composition which upon application to the lips forms a barrier layer over a base coat layer, which composition comprises A) from about 50% to about 85% of a first material which comprises
  i) wax selected from the group consisting of candelilla, ozokerite, paraffin, carnauba wax, and mixtures thereof;
  ii) combination of said wax with non-volatile oil selected from the group consisting of caprylic triglycerides, capric triglycerides, isostearic triglycerides, castor oil, adipic triglyceride, dimethicones, octyl dodecanol, oleyl alcohol, hydrogenated vegetable oils, maleated soybeam oil, lanolin oil, polybutenes, hexadecyl alcohol, wheat germ glycerides, and mixtures thereof; or
  iii) combination of said wax/non-volatile oil combination with volatile oil having a vapor pressure greater than about 10 mm Hg at 30° C. and selected from the group consisting of volatile hydrocarbons, poly (dimethylsiloxanes), cyclic poly(dimethylsiloxanes), and mixtures thereof; and B) from about 15% to about 50% of a second material which is incompatible with said first material within said lipstick composition, which has a viscosity of from about 10 to 100 centistokes and which is
  i) non-volatile material selected from the group consisting of polydimethylsiloxane fluids, poly (phenylmethylsiloxane) fluids, poly (fluoroalkylmethylsiloxane) fluids, perfluoropolyethers and mixtures thereof; and and wherein said second material is incompatible with said first material and is entrapped in said first material and wherein said composition is free of surfactants that would sufficiently stabilize the second material entrapped within the first material.

18. The composition of claim 17, further comprising a volatile fluid selected from the group consisting of volatile hydrocarbons and cyclomethicones.

19. The composition according to claim 1 wherein the second material has a viscosity of from about 10 to about 100 centistokes.

* * * * *

UNITED STATES PATENT AND TRADEMARK OFFICE
CERTIFICATE OF CORRECTION

PATENT NO. : 6,482,398 B1
DATED : November 19, 2002
INVENTOR(S) : Rabe et al.

It is certified that error appears in the above-identified patent and that said Letters Patent is hereby corrected as shown below:

Column 2,
Line 8, the first occurrence of "was" should read -- wax --.
Line 8, the second occurrence of "was" should read -- wax --.
Line 24, "Corporation," should read -- Corporation. --.
Line 38, "carbauba" should read -- carnauba --.
Line 44, "carnanuba" should read -- carnauba --
Line 44, "oxokerite" should read -- ozokerite --.
Line 45, "silicon" should read -- silicone --.
Line 63, "hyrodcarbons" should read -- hydrocarbons --.

Column 3,
Line 16, "oils," should read -- oils; --.
Line 21, "soybeam" should read -- soybean --.
Line 37, "1998" should read -- 1988 --.
Line 39, "Comsetic" should read -- Cosmetic --.
Line 43, "isopropoyl" should read -- isopropyl --.
Line 51, "pentaerythirtyl" should read -- pentaerythrityl --.
Line 58, "mixture" should read -- mixtures --.

Column 4,
Line 9, "material" should read -- materials --.
Line 14, "distriution" should read -- distribution --.
Line 26, after the word "material." insert the text -- In fact, some of the materials selected as either the first or second material may partition between the --.

Column 5,
Line 1, after the word "said" insert -- second --.
Line 12, "for" should read -- after --.
Line 64, "grousp" should read -- groups --.

Column 6,
Lines 8 and 9, "alkyl" should read -- allyl --.
Line 20, "(dimethylsiloxiane)" should read -- (dimethylsiloxane) --.
Lines 45-46, "compositions" should read -- composition --.

Column 7,
Line 11, after the word "second" insert -- material. --.

UNITED STATES PATENT AND TRADEMARK OFFICE
CERTIFICATE OF CORRECTION

PATENT NO. : 6,482,398 B1
DATED : November 19, 2002
INVENTOR(S) : Rabe et al.

It is certified that error appears in the above-identified patent and that said Letters Patent is hereby corrected as shown below:

Column 10,
Line 23, "and" should read -- are --.
Line 25, "are" should read -- and --.

Column 12,
Line 3, "the mixing" should read -- mixing --.
Line 6, "mintues" should read -- minutes --.
Line 54, "triglcerides" should read -- triglycerides --.
Line 56, "hydrogentated" should read -- hydrogenated --.
Lines 56-57, "soybeam" should read -- soybean --.
Lines 61-62, "mixture" should read -- mixtures --.

Column 14,
Line 9, "triglyceride" should read -- triglycerides --.
Line 11, "soybeam" should read -- soybean --.

Signed and Sealed this

Twenty-ninth Day of April, 2003

JAMES E. ROGAN
*Director of the United States Patent and Trademark Office*